(12) United States Patent
Dace et al.

(10) Patent No.: US 8,911,441 B2
(45) Date of Patent: Dec. 16, 2014

(54) ENDPLATE PREPARATION INSTRUMENTS AND METHODS OF USE

(75) Inventors: Mark Dace, Memphis, TN (US); Stephen Papadopoulos, Paradise Valley, AZ (US); Stephen White, Memphis, TN (US); Bradley Coates, Yarmouth, IA (US); Greg Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1467 days.

(21) Appl. No.: 12/244,825

(22) Filed: Oct. 3, 2008

(65) Prior Publication Data

US 2010/0087830 A1    Apr. 8, 2010

(51) Int. Cl.
| | |
|---|---|
| A61B 17/00 | (2006.01) |
| A61B 17/16 | (2006.01) |
| A61B 17/70 | (2006.01) |
| A61B 17/02 | (2006.01) |
| A61B 19/00 | (2006.01) |

(52) U.S. Cl.
CPC ......... *A61B 17/1671* (2013.01); *A61B 17/7077* (2013.01); *A61B 2017/0256* (2013.01); *A61B 2017/1602* (2013.01); *A61B 2019/306* (2013.01)
USPC .......................................................... 606/84

(58) Field of Classification Search
USPC ............. 606/79, 80, 81, 82, 84, 85, 167, 171, 606/172, 176–180
See application file for complete search history.

(56) References Cited

U.S. PATENT DOCUMENTS

| | | | |
|---|---|---|---|
| 4,842,578 A | | 6/1989 | Johnson et al. |
| 5,376,092 A | * | 12/1994 | Hein et al. ................... 606/81 |
| 5,387,215 A | | 2/1995 | Fisher |
| 5,569,285 A | * | 10/1996 | Webb ........................... 606/180 |
| 5,913,867 A | * | 6/1999 | Dion ............................ 606/180 |
| 6,063,088 A | | 5/2000 | Winslow |
| 6,083,228 A | | 7/2000 | Michelson |
| 6,120,506 A | | 9/2000 | Kohrs et al. |
| 6,221,076 B1 | * | 4/2001 | Albrektsson et al. ......... 606/80 |
| 6,245,074 B1 | * | 6/2001 | Allard et al. ................. 606/80 |
| 6,440,139 B2 | | 8/2002 | Michelson |
| 6,966,912 B2 | | 11/2005 | Michelson |
| 7,083,623 B2 | | 8/2006 | Michelson |
| 7,083,625 B2 | | 8/2006 | Berry |
| 7,147,642 B2 | | 12/2006 | Grinberg et al. |
| 2002/0111631 A1 | * | 8/2002 | Gil et al. ....................... 606/79 |
| 2003/0130662 A1 | * | 7/2003 | Michelson .................... 606/79 |
| 2003/0181915 A1 | * | 9/2003 | Serhan ......................... 606/79 |
| 2003/0187448 A1 | * | 10/2003 | Michelson .................... 606/79 |
| 2004/0162563 A1 | * | 8/2004 | Michelson .................... 606/79 |
| 2005/0015091 A1 | * | 1/2005 | Bryan et al. .................. 606/80 |
| 2005/0165420 A1 | * | 7/2005 | Cha .............................. 606/150 |
| 2005/0273111 A1 | | 12/2005 | Ferree et al. |

(Continued)

*Primary Examiner* — Christian Sevilla

(57) ABSTRACT

The present application is directed to instruments and methods for preparing a space between vertebral members. One embodiment of the instrument may include an elongated shaft with a proximal end and a distal end. A blade may be positioned at an end of the shaft and may rotate about an axis. The blade may include one or more teeth that include a height and/or contour. During rotation of the blade, the teeth contact and cut into one of the vertebral members. The instrument may also include a depth stop that limits a depth that the teeth can cut into the vertebral member. In some embodiments, the instrument includes a second blade that is configured to cut into the second vertebral member.

20 Claims, 7 Drawing Sheets

(56) References Cited

U.S. PATENT DOCUMENTS

2006/0129160 A1  6/2006  Liu et al.
2006/0241626 A1  10/2006  McGahan et al.
2007/0233130 A1* 10/2007  Suddaby .................. 606/79
2007/0288029 A1  12/2007  Justin et al.

* cited by examiner

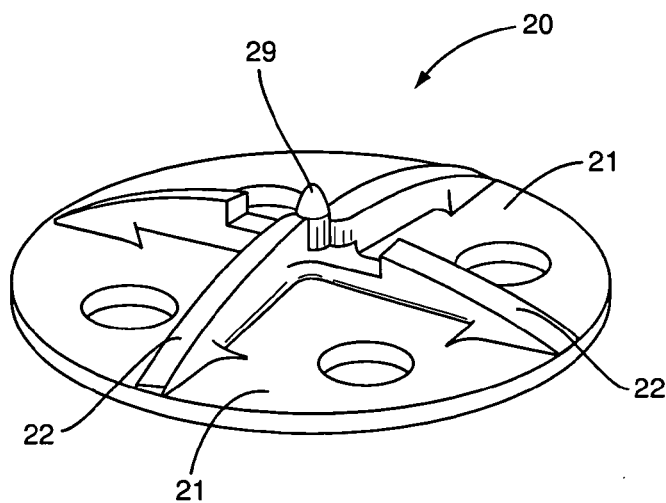
FIG. 10
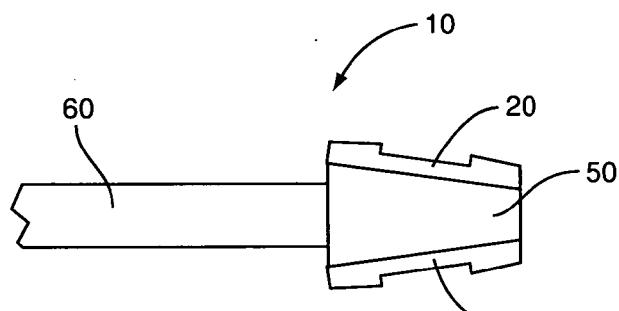
FIG. 11
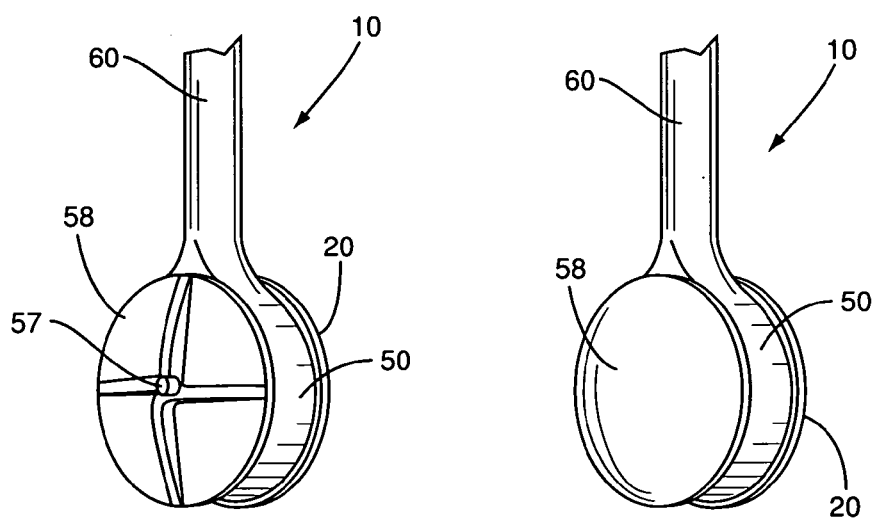
FIG. 12   FIG. 13

ENDPLATE PREPARATION INSTRUMENTS AND METHODS OF USE

BACKGROUND

The present application relates generally to medical instruments and methods of use and, particularly, to medical instruments and methods for contouring one or more vertebral endplates.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs. The damage may result from a variety of causes including a specific event such as trauma, a degenerative condition, a tumor, or infection. Damage to the intervertebral discs and vertebral members can lead to pain, neurological deficit, and/or change of motion.

Various procedures include replacing and/or repairing all or part of an intervertebral disc. These procedures often require contouring one or more of the endplates of the vertebral members. The contouring prepares the endplates to receive an intervertebral implant.

SUMMARY

The present application is directed to instruments and methods for preparing a space between vertebral members. One embodiment of the instrument may include an elongated shaft with a proximal end and a distal end. A blade may be positioned at an end of the shaft and may rotate about an axis. The blade may include one or more teeth that include a height and/or contour. During rotation of the blade, the teeth contact and cut into one of the vertebral members. The instrument may also include a depth stop that limits a depth that the teeth can cut into the vertebral member. In some embodiments, the instrument includes a second blade that is configured to cut into the second vertebral member.

BRIEF DESCRIPTION OF THE DRAWINGS

FIG. 10 is a perspective view of a blade according to one embodiment.

FIG. 11 is a side schematic view of a pair of blades aligned relative to a shaft according to one embodiment.

FIG. 12 is perspective view of a backside of a housing according to one embodiment.

FIG. 13 is perspective view of a backside of a housing according to one embodiment.

DETAILED DESCRIPTION

Figure 1:
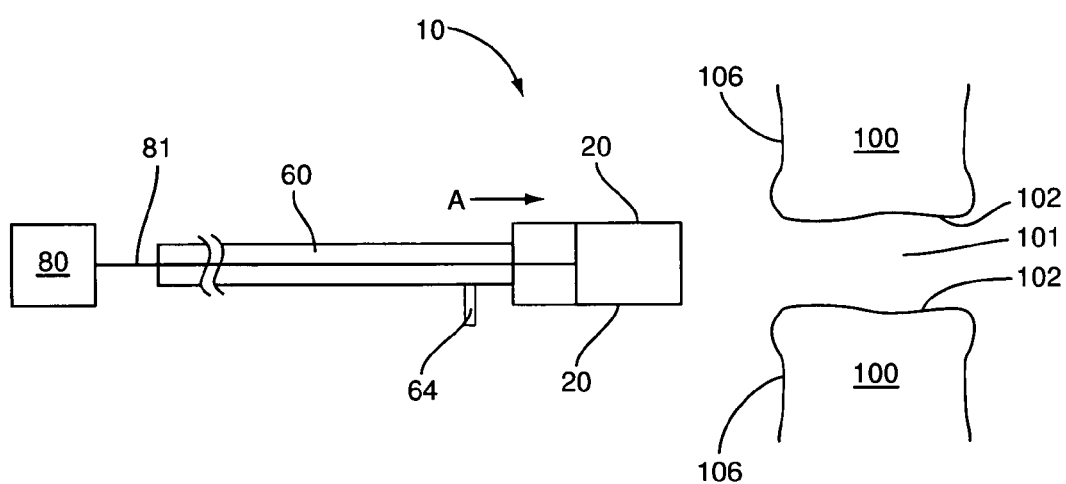
FIG. 1 is a schematic diagram of an instrument positioned in proximity to vertebral members according to one embodiment.

The present application is directed to instruments and methods for contouring endplates of one or more vertebral members. FIG. 1 illustrates a schematic view of one embodiment of an instrument 10 that includes one or more blades 20 positioned at an end of a shaft 60. The instrument 10 is sized to be inserted in the direction of arrow A and fit within the disc space 101. Once inserted, the blades 20 are brought into vertical contact with the endplates 102 of the vertebral members 100. Rotation of the blades 20 causes the endplates 102 to be contoured to an appropriate shape. A depth stop controls a depth that the blades 20 can vertically cut into the endplates 102.

Figure 2:
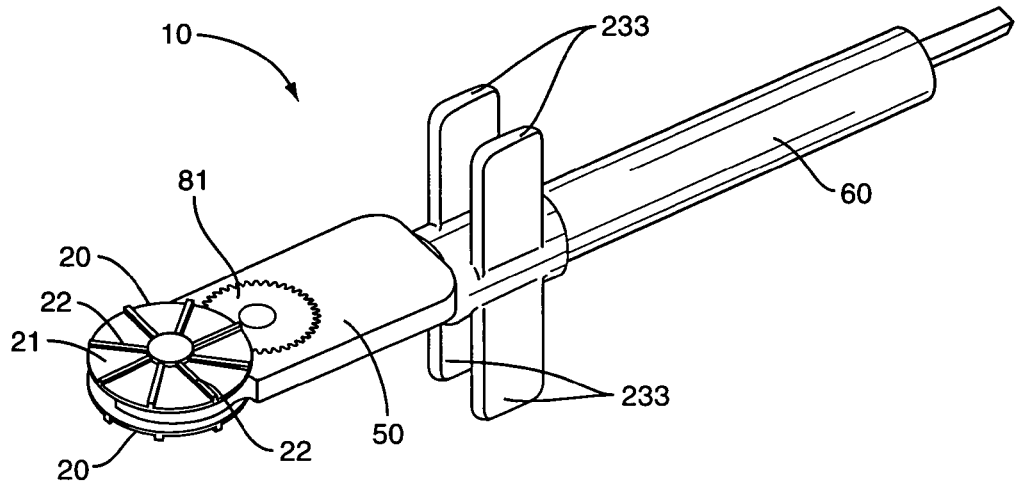
FIG. 2 is a perspective view of an instrument according to one embodiment.

FIG. 2 illustrates a perspective view of one embodiment of an instrument 10. The blades 20 are mounted on a housing 50 positioned at a distal end of the shaft 60. The blades 20 may be rotated about an axis that is transverse to a longitudinal axis of the shaft 60. This may include the rotational axis being perpendicular to the longitudinal axis, or at a variety of various angles.

The blades 20 may include various geometries to match the required contouring of the endplates 102. Each blade 20 includes a base 21 and one or more teeth 22. The base 21 provides a foundation for the teeth 22. In one embodiment, the base 21 is substantially smooth to provide a non-cutting surface as will be explained below. The surface of the base 21 may be flat, or may include a curved configuration. Base 21 may include a variety of shapes, including but not limited to circular, rectangular, and triangular.

The teeth 22 extend outward from the base 21 and are configured to cut into the endplate 102 during rotation of the blade 20. The teeth 22 include a height measured between the base 21 and a tip of the teeth 22. Each tooth 22 may include the same height, or the various teeth 22 may include different heights.

Figure 3:
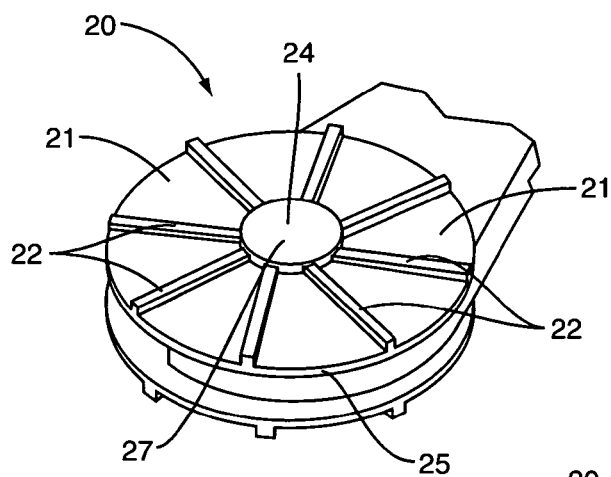
FIG. 3 is a perspective view of a blade according to one embodiment.
Figure 4:
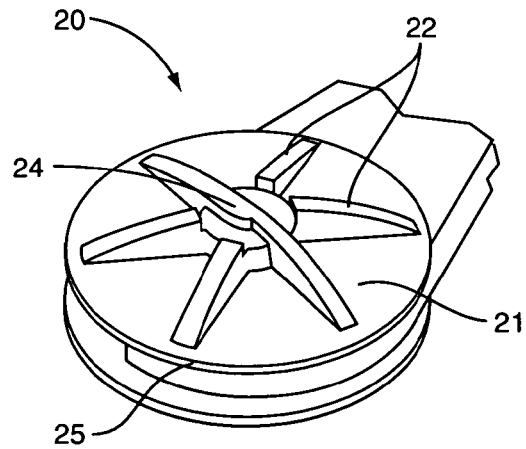
FIG. 4 is a perspective view of a blade according to one embodiment.

The shape of the teeth 22 may vary depending upon the desired contouring. FIG. 3 illustrates one embodiment with the teeth 22 including an elongated shape positioned to extend outward from a central area near a center 24 of the base 21 to a peripheral edge 25 of the base 21. In this embodiment, the teeth 22 include a substantially constant height along their length. FIG. 4 includes another embodiment with elongated teeth 22 extending outward from the center 24. The height of the teeth 22 decreases away from the center 24, and the teeth 22 do not extend entirely to the edge 25 of the base 21. FIG.

Figure 6:
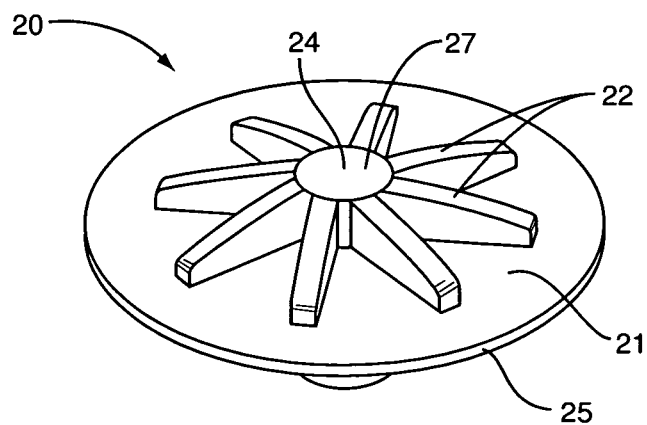
FIG. 6 is a perspective view of a blade according to one embodiment.

5 includes an embodiment with a plurality of teeth 22 positioned along the edge 25 of the base 21. FIG. 6 includes another embodiment with a plurality of elongated teeth 22 extending outward from a central area in proximity to the center 24.

One or more depth stops are associated with each blade 20 to control a depth that the one or more teeth 22 can cut into the vertebral member 100. The depth stop may include one or more of the base 21, housing 50, and a non-cutting area 27 that extends outward from the base 21. The depth stop includes a surface that does not cut into the vertebral member 100 when placed in contact with the vertebral member 100. In one specific embodiment, the depth stop is smooth.

The base 21 may act as a stop to control a depth that the teeth 22 cut into the endplates 102. In use, the blade 20 is inserted into the disc space 101 with the teeth 22 contacting against the endplates 102 of the vertebral members 100. Rotation of the blade 20 causes the teeth 22 to cut into the endplates 102. After a predetermined amount of cutting, the teeth 22 have contoured the endplates 102 to a predetermined shape and depth. The base 21 contacts against the endplate 102 and prevents the teeth 22 from further cutting into the endplates 102.

The non-cutting area 27 may act as the depth stop. The non-cutting area 27 includes a height to extend outward from the base 21 as illustrated in FIGS. 3 and 6. In each of these embodiments, the non-cutting areas 27 are positioned at the center 24 of the blade 20. In other embodiments, the non-cutting areas 27 are positioned away from the center 24 of the blade 20. Further, blades 20 may include a single non-cutting area 27, or multiple non-cutting areas 27. The height of the non-cutting area 27 may be the same throughout, or may vary. In one embodiment, the non-cutting area 27 includes a dome shape with a maximum height at a center and decreasing heights around the edges. The non-cutting area 27 may include a symmetrical or non-symmetrical shape. In use, the blade 20 contacts against the endplate 102 of the vertebral member 100. Initially, the teeth 22 contact against and cut the endplate 102 with the non-cutting area 27 being spaced away from the endplate 102. Eventually, the teeth 22 cut into the endplate 102 a depth that moves the non-cutting area 27 into contact with the endplate 102. This prevents the teeth 22 from cutting farther into the endplate 102.

Figure 7A:
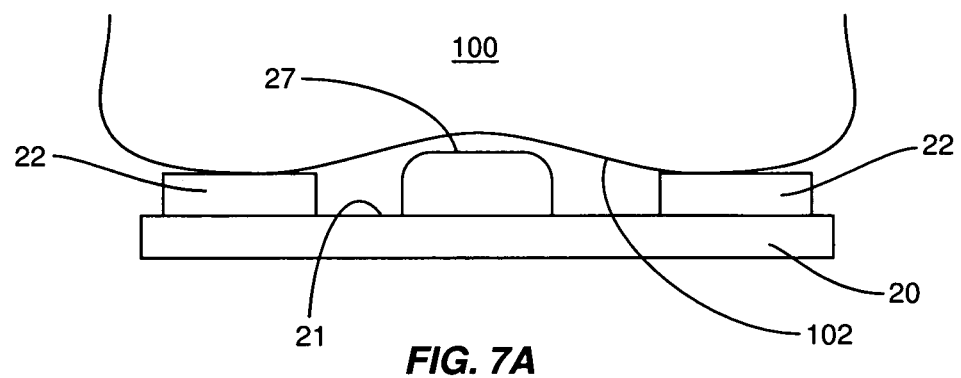
FIG. 7A is a side schematic view of a blade contouring a vertebral member a first amount according to one embodiment.
Figure 7B:
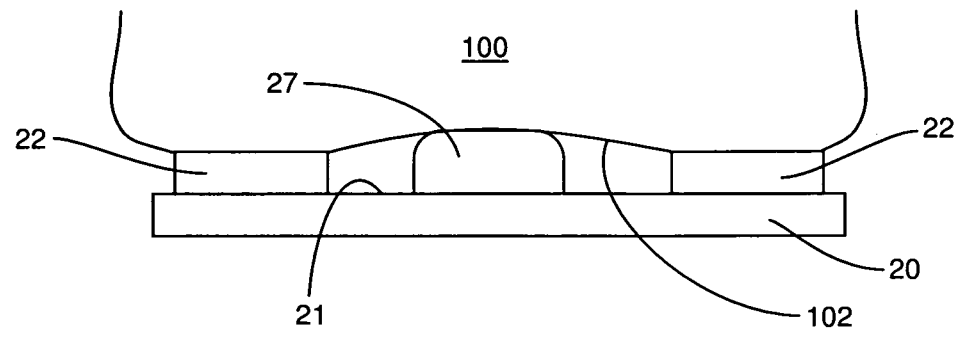
FIG. 7B is a side schematic view of a blade with a non-cutting area contacting a vertebral member according to one embodiment.

FIGS. 7A and 7B schematically illustrate one embodiment of a blade 20 cutting into a vertebral member 100. FIG. 7A illustrates the blade 20 and endplate 102 making vertical contact. The endplate 102 includes a concave shape with a central section spaced further away from the blade 20 than the peripheral edges. The non-cutting area 27 is positioned at the center 24 of the blade 20 and aligns with the concave central section of the endplate 102. The shape of the endplate 102 and the shape of the blade 20 provides for the teeth 22 on the periphery of the blade 20 to cut into the endplate 102 while the non-cutting area 27 remains positioned away from the endplate 102. As illustrated in FIG. 7B, the teeth 22 cut into the vertebral member 100 a depth that places the non-cutting area 27 into contact with the endplate 102. This contact then prevents further cutting by the teeth 22.

Figure 8:
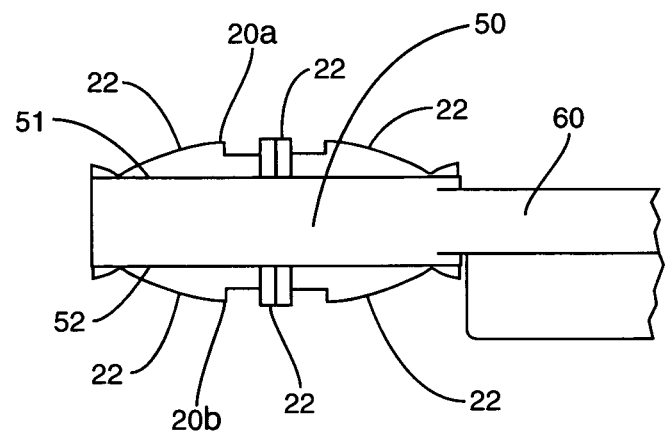
FIG. 8 is a side view of an instrument with a pair of blades according to one embodiment.

The inserter housing 50 may also control the depth of the contouring. As illustrated in the embodiments of FIGS. 2 and 8, the blades 20 are positioned at the distal end of the shaft 60. The blades 20 are positioned with one or more teeth 22 extending outward above the housing 50. As best illustrated in FIG. 8, the teeth 22 on the first blade 20a extend outward beyond the first contact surface 51, and the teeth 22 on the second blade 20b extend outward beyond the second contact surface 52. During contouring, the teeth 22 cut into the endplates 102 on each side of the housing 50. The first blade 20a cuts into the first endplate 102 a depth until the endplate 102 contacts against the first contact surface 51. Likewise, the second blade 20b cuts into the second endplate 102 until the second contact surface 52 contacts against the endplate 102. In one embodiment, one or both of the contact surfaces 51, 52 are positioned between a tip of the teeth 22 and the bases of each blade 20a, 20b. In another embodiment, the bases 21 of the blades 20a, 20b are aligned with the contact surfaces 51, 52, respectively.

The housing 50 may extend completely or partially around a periphery of one or both blades 20. Further, each of the blades 20a, 20b may extend the same or different distances from their respective contact surfaces 51, 52. By way of example, the teeth 22 on the first blade 20a may extend above the contact surface 51 a greater amount than the teeth 22 on the second blade 20b extend above the contact surface 52.

Figure 9:
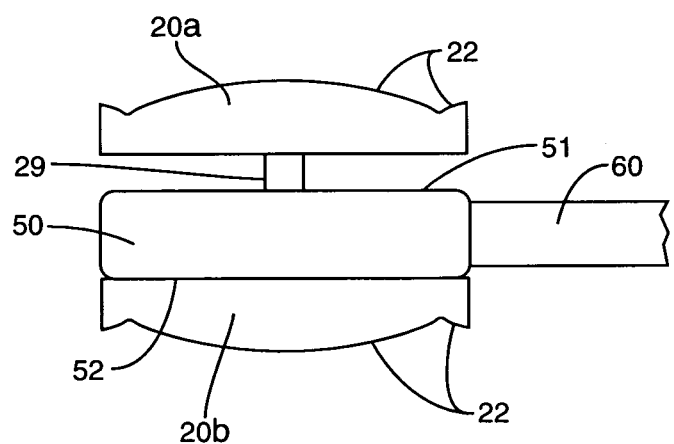
FIG. 9 is a side view of an instrument with a pair of blades according to one embodiment.

FIG. 9 illustrates an embodiment with blade 20a including an extension 28. The extension 28 is operatively connected to the housing 50 and includes a length such that a lower edge of the blade 20a is positioned outward and away from the contact surface 51. The extension 28 may be centered on the blade 20a. In this embodiment, a second blade 20b without an extension is positioned on an opposite side of the housing 50.

As illustrated in FIG. 10, blade 20 may also include a spike 29 that provides stability to the instrument 10 during contouring of the one or more vertebral members 100. The spike 29 includes a pointed end that extends above the teeth 22 and contacts against the endplate 102. During rotation of the blade 20, the spike 29 engages the endplate 102 to stabilize the instrument 10 and prevent lateral movement.

The blades 20 may be positioned at a variety of angles relative to each other. In one embodiment as illustrated in FIGS. 8 and 9, the blades 20 are substantially parallel. In another embodiment as schematically illustrated in FIG. 11, blades 20 are positioned at an angle relative to each other. The degree of the angle may be selected to match the lordotic curvature at the level of the spine that is being contoured. The distance between the blades 20 may also vary depending upon the height of the disc space 101.

In the embodiments discuss above, the instrument 10 includes a pair of blades 20. A first blade may be positioned on a first side of a longitudinal axis of the shaft 60, and a second blade is positioned on a second side. The blades 20 face in opposite directions to contour separate vertebral members 100. The instrument 10 may also include a single blade 20 as illustrated in the embodiments of FIGS. 12 and 13. These embodiments includes a housing 50 positioned at a distal end of the shaft 60. A single blade 20 is positioned on one side of the housing 50. A backside 58 of the housing 50 may be shaped to contact against a vertebral member 100 and place the blade 20 in position for contouring. The backside 58 may include one or more spikes 57 to maintain the position of the instrument relative to the vertebral member 100. The geometry of the backside 58 may vary, such as an overall convex shape as illustrated in FIG. 12, and substantially flat as illustrated in FIG. 13. The blade 20 may be positioned at various angles relative to the backside 58 as dictated by the desired contouring of the vertebral member 100, and/or the shape and size of the disc space 101.

The shaft 60 includes an elongated shape for stabilizing a blade 20 within the disc space 101 and against the vertebral member 100. In one embodiment as illustrated in FIG. 1, a stop 64 may extend outward from one or more sides of the shaft 60 to contact against a vertebral member 100 and control an amount of insertion into the disc space 101.

A drive mechanism 80 functions to rotate the blades 20 as schematically illustrated in FIG. 1. The drive mechanism 80 may be positioned within the housing 50, within the shaft 60, or distanced away from the shaft 60 and operatively connected to the blades 20 through conduit 81. Conduit 81 may include a variety of forms, including a gear train or a tube. The drive mechanism 80 may power the blades 20 to continuously rotate in one direction, or may cause the blades 20 to oscillate with rotational movement in a first direction followed by rotational movement in a second direction. In a two-blade instrument 10, the drive mechanism 80 may be configured to concurrently drive both blades 20, or to individually drive the blades 20 such that one blade 20 rotates while the second blade 20 is stationary. This allows for the instrument 10 to be used to concurrently contour two vertebral members 100, or just a single vertebral member 100. In a two-blade instrument 10 with rotational blades 20, the blades 20 may rotate in the same or opposite directions. The drive mechanism 80 may include but is not limited to a battery, electrical motor, magnetic driver, cam mechanism, and gas powered turbine element. U.S. Pat. No. 6,966,912 discloses various drive mechanisms and is herein incorporated by reference.

Figure 15:
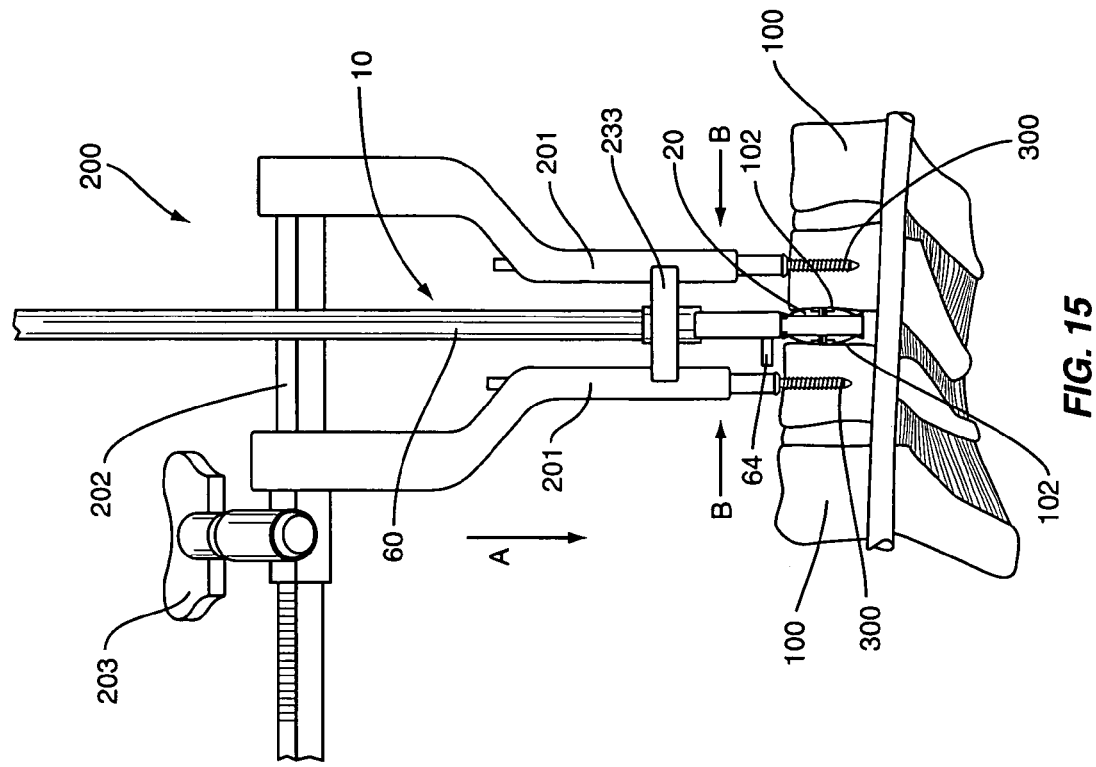
FIG. 15 is a side view of an instrument engaged with a distraction mechanism and blades positioned within a disc space according to one embodiment.
Figure 14:
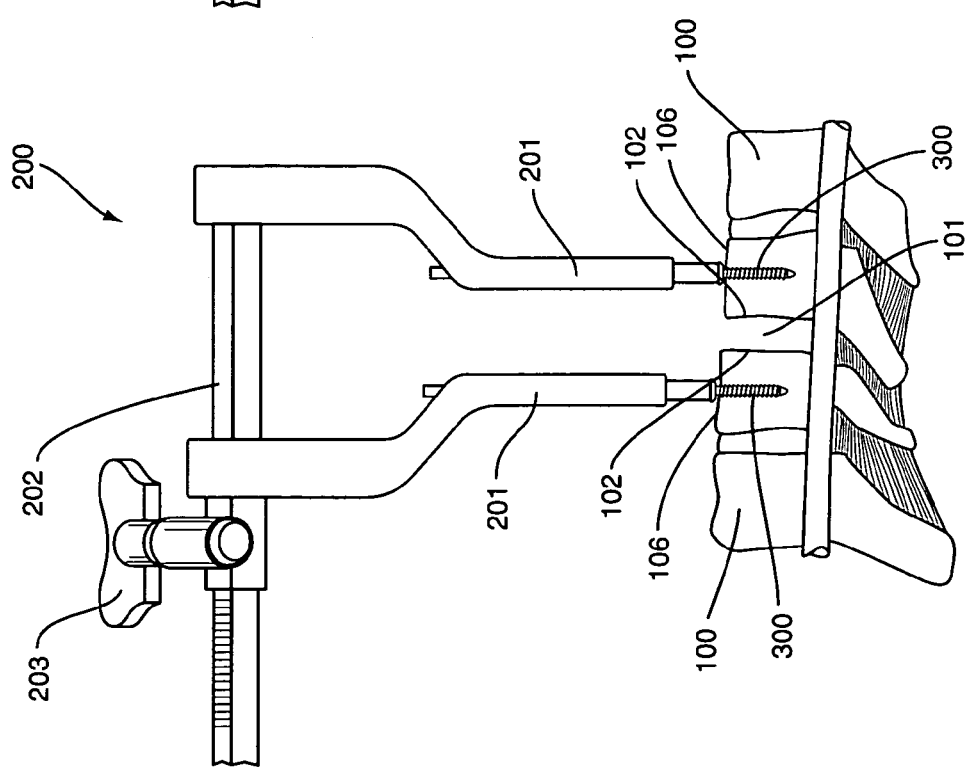
FIG. 14 is a side view of a distraction mechanism attached to vertebral members according to one embodiment.

FIGS. 14-15 illustrate one embodiment of using an instrument 10 to contour endplates 102 of vertebral members 100. As illustrated in FIG. 14, a distraction mechanism 200 may be initially attached to the vertebral members 100. In this embodiment, the distraction mechanism 200 includes a pair of arms 201 that are mounted on an intermediate brace 202. An adjustment mechanism 203 may be positioned along the brace 202 to adjust a distance between the arms 201.

The distraction mechanism 200 may be attached to the vertebral members 100 through fasteners 300. The fasteners 300 are attached to the anterior surfaces 106 of the vertebral members 100, and the distal ends of the arms 201 are attached to the fasteners 300.

The size of the disc space 101 may be determined prior to or after attached of the distraction mechanism 200. The size may be used to determine the appropriate size of instrument 10 necessary to contour the vertebral members 100.

As illustrated in FIG. 15, the instrument 10 is aligned with the distraction mechanism 200. In one embodiment, the shaft 60 of the instrument 10 includes orthogonal members (see FIG. 2) that are spaced to engage with the arms 201. In one embodiment, the orthogonal members 233 form an H-bracket to engage each of the arms 201 and provide for accurate placement of the blades 20 within the disc space 101.

The instrument 10 is inserted along the arms 201 and into the disc space 101 as illustrated by arrow A. Once inserted, the blades 20 are accurately aligned within the disc space 101. After alignment, the blades 20 are brought into contact with the endplates 102 of the vertebral members 100. This contacting movement may be caused by a vertical movement of the vertebral members 100 as illustrated by arrows B. In one embodiment, the vertebral members 100 are distracted prior to insertion of the blades 20. After insertion, the vertebral members are moved together such that the endplates 102 are moved into contact with the blades 20. In another embodiment, the blades 20 are vertically engaged by the surgeon against the endplates 102. As the blades 20 contact the endplates 102, the teeth 20 cut into the endplates 102. The depth of the cuts is limited due to contact with the depth stops. The depth stops may contact a non-cut section of the vertebral members 100.

In one embodiment, the contouring occurs one side at a time. A first blade 20 contacts against and contours a first vertebral member 100, followed by a second blade 20 contacting and contouring a second vertebral member 100.

Figure 5:
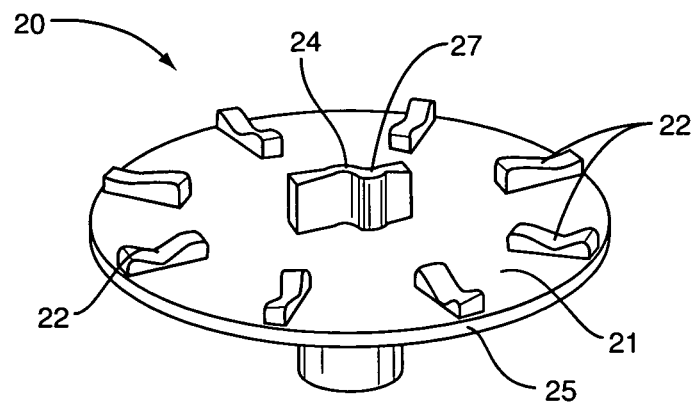
FIG. 5 is a perspective view of a blade according to one embodiment.

Once the contouring is complete, the blades 20 are removed from the disc space 101. This may be performed by sliding the instrument 10 outward along the arms 201. In one embodiment, the one or more blades 20 originally attached to the instrument 10 at the time of insertion is adequate to contour the disc space 101. Once complete, a spacer is inserted into the contoured disc space 101. In another embodiment, the contouring is performed in two or more stages. A first type of blade 20 is initially attached to the instrument 10 to contour the endplates 102 a first amount. Once complete, a second type of blade 20 is moved into the disc space 101 to contour the endplates 102 a second amount. Additional blades 20 may be inserted into the disc space 101 as necessary to perform any additional contouring. In one embodiment, the first blade 20 includes a first set of teeth as illustrated in the blade 20 of FIG. 5, and a second blade 20 includes a second set of teeth as illustrated in blade 20 of FIG. 6.

In another embodiment, the instrument 10 is used with no distraction of the vertebral members 100. In use, the instrument 10 is manipulated to position the one or more blades 20 within the disc space 101. Once in position, the one or more blades 20 contact against and contour the one or more vertebral members 100. Afterward contouring, the one or more blades 20 are removed from the disc space 101.

In one embodiment, the instrument 10 is repeatedly moved up and down along the distraction mechanism 200 to move the blade 20 into and out of the disc space. The engagement between the orthogonal members 233 and the arms 201 of the distraction mechanism 200 allows of this repeated movement and for accurate alignment of the blade 20 within the disc space 20 during each insertion and removal step.

The instrument 10 may be inserted into the disc space 101 from a variety of directions. In one embodiment, the instrument 10 is inserted in an anterior approach. Other applications contemplate other approaches, including posterior, postero-lateral, antero-lateral and lateral approaches to the disc space 101. Further, the instrument 10 may be used to contour vertebral members 100 within various regions of the spine, including the cervical, thoracic, lumbar and sacral portions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment, the instrument 10 does not include a housing 50 and the one or more blades 20 are connected to the shaft 60. In one embodiment, the orthogonal members 233 act as a stop to control an extent of insertion of the blades 20 into the disc space 101. The present embodiments are, therefore, to be considered in all respects as illustrative and not restrictive, and all changes coming within the meaning and equivalency range of the appended claims are intended to be embraced therein.

What is claimed is:

1. An instrument to prepare a space between vertebral members comprising:
   a shaft including a proximal end and a distal end;
   a blade rotationally mounted at the distal end of the shaft and rotating about an axis that is transverse to a longitudinal axis of the shaft, the blade including a base and a plurality of spaced apart teeth that each extend outward from the base such that each of the plurality of teeth are disposed at an acute angle relative to an adjacent tooth, each of the plurality of teeth extending from a center of the blade and terminating prior to a peripheral edge of the base, each of the plurality of teeth having a height measured between the base and a tip and being configured to cut into one of the vertebral members; and
   a depth stop positioned at the center of the blade, the depth stop extending outward from the base of the blade in a same direction as each of the plurality of teeth, wherein the depth stop includes a non-cutting surface positioned relative to the tips of each of the plurality of teeth to limit the cut to a depth that is less than the height of each of the plurality of the spaced apart teeth.

2. The instrument of claim 1, wherein the distal end of the shaft includes a housing that receives the blade.

3. The instrument of claim 2, wherein the housing extends completely around a periphery of the blade.

4. The instrument of claim 1, further comprising a second blade positioned on an opposite side of the longitudinal axis from the blade, the second blade adapted to cut into the second vertebral member.

5. An instrument to prepare a space between vertebral members comprising:
   a shaft including a distal end and a proximal end;
   a blade rotationally mounted at the distal end of the shaft and rotating about an axis that is transverse to a longitudinal axis of the shaft, the blade including a base and a plurality of spaced apart teeth that each extend outward from the base, each of the plurality of teeth including a tip to cut into one of the vertebral members, the blade further including a non-cutting area that is devoid of teeth and extends outward from the base in a same direction as each of the plurality of teeth, the non-cutting area being centered about the rotational axis of the blade;
   wherein the plurality of teeth each include an elongated shape that extends radially outward from the non-cutting area and terminates prior to a peripheral edge of the base and each of the plurality of teeth are disposed at an acute angle relative to an adjacent tooth.

6. The instrument of claim 5, further comprising a second blade mounted at the distal end of the shaft and positioned on an opposite side of the longitudinal axis from the blade, the second blade adapted to cut into the second vertebral member.

7. The instrument of claim 5, wherein a height of the non-cutting area is greater than each of the plurality of teeth.

8. The instrument of claim 1, wherein none of the plurality of teeth extend parallel to another of the plurality of teeth.

9. The instrument of claim 1, wherein the height of each of the plurality of teeth decreases away from the center.

10. The instrument of claim 1, wherein:
    each of the plurality of teeth include a first end that engages the depth stop and an opposite second end; and
    each of the plurality of teeth are tapered continuously from the first end to the second end.

11. The instrument of claim 1, wherein the height of one of the plurality of teeth is different than the height of another one of the plurality of teeth.

12. The instrument of claim 1, wherein the depth stop is permanently fixed to the base.

13. The instrument of claim 1, wherein the non-cutting surface has a dome shape.

14. The instrument of claim 1, wherein:
    the instrument comprises a distraction mechanism comprising a pair of arms; and
    the shaft comprises a plurality of orthogonal members that form an H-bracket that engages each of the arms.

15. The instrument of claim 1, wherein the shaft comprises a stop extending perpendicular to the longitudinal axis of the shaft from one or more sides of the shaft configured to contact against one of the vertebral members to control an amount of insertion into a disc space.

16. The instrument of claim 1, wherein:
    the instrument comprises a second blade positioned on an opposite side of the longitudinal axis; and
    the blade rotates while the second blade is stationary.

17. The instrument of claim 1, wherein:
    the instrument comprises a second blade positioned on an opposite side of the longitudinal axis; and
    the blade and the second blade both rotate in a first direction simultaneously.

18. The instrument of claim 1, wherein:
    the instrument comprises a second blade positioned on an opposite side of the longitudinal axis; and
    the blade rotates in a first direction while the second blade rotates in a second direction that is opposite the first direction.

19. The instrument of claim 1, wherein:
    the instrument comprises a second blade positioned on an opposite side of the longitudinal axis; and
    the second blade comprises a plurality of second teeth such that the plurality of second teeth have a configuration that is identical to that of the plurality of teeth.

20. The instrument of claim 1, wherein:
    the instrument comprises a second blade positioned on an opposite side of the longitudinal axis; and
    the blade extends parallel to the second blade.

* * * * *